(12) United States Patent
Stiehl

(10) Patent No.: US 9,017,335 B2
(45) Date of Patent: Apr. 28, 2015

(54) HIP IMPLANT REGISTRATION IN COMPUTER ASSISTED SURGERY

(75) Inventor: James B. Stiehl, Salem, IL (US)

(73) Assignee: Blue Ortho, La Tronche (FR)

( * ) Notice: Subject to any disclaimer, the term of this patent is extended or adjusted under 35 U.S.C. 154(b) by 239 days.

(21) Appl. No.: 12/742,909

(22) PCT Filed: Nov. 19, 2008

(86) PCT No.: PCT/US2008/012970
§ 371 (c)(1),
(2), (4) Date: May 13, 2010

(87) PCT Pub. No.: WO2009/067235
PCT Pub. Date: May 28, 2009

(65) Prior Publication Data
US 2010/0261998 A1     Oct. 14, 2010

Related U.S. Application Data

(60) Provisional application No. 60/989,103, filed on Nov. 19, 2007.

(51) Int. Cl.
| | |
|---|---|
| A61F 2/46 | (2006.01) |
| A61B 19/00 | (2006.01) |
| A61F 2/32 | (2006.01) |

(52) U.S. Cl.
CPC .............. *A61B 19/50* (2013.01); *A61B 19/5244* (2013.01); *A61B 2019/508* (2013.01); *A61B 2019/5255* (2013.01); *A61F 2/32* (2013.01)

(58) Field of Classification Search
USPC ......... 606/86 R, 89, 91, 102, 130; 623/20.35, 623/22.11, 22.12, 22.21, 23.11, 908, 914; 600/424–429, 587, 594
See application file for complete search history.

(56) References Cited

U.S. PATENT DOCUMENTS

| | | |
|---|---|---|
| 5,251,127 A | 10/1993 | Raab |
| 5,305,203 A | 4/1994 | Raab |

(Continued)

FOREIGN PATENT DOCUMENTS

WO    WO 2007/095248    8/2007

OTHER PUBLICATIONS

Haaker et al., Comparison of Conventional Versus Computer-Navigated Acetabular Component Insertion, The Journal of Arthroplasty, vol. 00 No. 0, 2005, pp. 1-8.

(Continued)

*Primary Examiner* — Andrew Yang
*Assistant Examiner* — Diana S Jones
(74) *Attorney, Agent, or Firm* — Blakely Sokoloff Taylor & Zafman

(57) ABSTRACT

A computer assisted surgical navigation system and method is disclosed for registering the position of prosthetic hip joint components. Elements are applied to the pelvis and femur, generating a three-dimensional array. These two arrays combine to derive a reference point representing the native joint. A tracking device with a pre-determined shape and dimensions that precisely articulate with an acetabular cup component generates a third three-dimensional array. The device has a further shape and dimensions that independently articulate precisely with a neck portion of a femoral component, which represents a prosthetic joint center that is independently registered in the system. The tracking device concurrently registers the three dimensional positions of the femoral and acetabular prosthetic components, along with the prosthetic joint center and the native joint center, respectively enabling alterations in three dimensional location of the leg length and offset prior to reduction of the prosthetic joint.

12 Claims, 6 Drawing Sheets

(56) References Cited

U.S. PATENT DOCUMENTS

| | | | |
|---|---|---|---|
| 5,682,886 | A | 11/1997 | Delp et al. |
| 5,871,018 | A | 2/1999 | Delp et al. |
| 5,995,738 | A | 11/1999 | DiGioia, III et al. |
| 6,340,363 | B1 | 1/2002 | Bolger et al. |
| 6,351,659 | B1 | 2/2002 | Vilsmeier |
| 6,450,978 | B1 | 9/2002 | Brosseau et al. |
| 6,533,737 | B1 | 3/2003 | Brosseau et al. |
| 6,551,325 | B2 | 4/2003 | Neubauer et al. |
| 6,685,711 | B2 | 2/2004 | Axelson, Jr. et al. |
| 6,991,655 | B2 | 1/2006 | Iversen |
| 7,029,477 | B2 | 4/2006 | Grimm |
| 7,419,492 | B2 | 9/2008 | Yoon et al. |
| 2002/0133160 | A1 | 9/2002 | Axelson, Jr. et al. |
| 2004/0044295 | A1 | 3/2004 | Reinert et al. |
| 2004/0092944 | A1* | 5/2004 | Penenberg ............... 606/91 |
| 2004/0097952 | A1* | 5/2004 | Sarin et al. ............... 606/102 |
| 2004/0143340 | A1* | 7/2004 | Tuma et al. ............ 623/22.12 |
| 2004/0147926 | A1 | 7/2004 | Iversen |
| 2004/0230199 | A1* | 11/2004 | Jansen et al. ............. 606/91 |
| 2004/0243148 | A1 | 12/2004 | Wasielewski |
| 2004/0254584 | A1* | 12/2004 | Sarin et al. ............... 606/102 |
| 2005/0021044 | A1 | 1/2005 | Stone et al. |
| 2005/0065617 | A1 | 3/2005 | Moctezuma de la Barrera et al. |
| 2005/0119661 | A1 | 6/2005 | Hodgson et al. |
| 2005/0203536 | A1 | 9/2005 | Laffargue et al. |
| 2005/0234468 | A1 | 10/2005 | Carson |
| 2006/0287613 | A1 | 12/2006 | Amiot et al. |
| 2007/0038223 | A1 | 2/2007 | Marquart et al. |
| 2007/0066917 | A1 | 3/2007 | Hodorek et al. |
| 2007/0100258 | A1 | 5/2007 | Shoham et al. |
| 2007/0162142 | A1 | 7/2007 | Stone |
| 2008/0009952 | A1 | 1/2008 | Hodge |
| 2008/0146969 | A1* | 6/2008 | Kurtz ....................... 600/595 |
| 2008/0214960 | A1 | 9/2008 | Hodgson et al. |

OTHER PUBLICATIONS

Murphy. S B., Alumina Ceramic-Ceramic Total Hip Arthoplasry Using Computer-Assisted Surgical Navigation and a New Minimally Invasive Technique, Advanced Ceramic Applications and New Projects, 9th Biolos Symposium, 2004, pp. 61-69.

Columbia St. Mary's Launches New Surgical Navigation for Orthopaedic Surgery, extracted from http://www.columbia-stmarys.org/NewsPressReleases.asp?PageID=WTN000096 on Oct. 15, 2008.

Buckup et al., Minimally Invasive Implantation and Computer Navigation for a Unicondylar Knee System, Ortho Supersite, http://www.orthosupersite.com/print.asp?rID=23132, Aug. 2007.

Stiehl et al., Computer-Assisted Surgery: Principles, Technology, extracted on Mar. 28, 2005, vol. 38, pp. 239-246.

Stiehl et al., Validation of Imageless Total Hip Navigation, Total Hip Arthroplasty, Part IV—42, extracted on Dec. 9, 2006, pp. 334-338.

Stiehl et al., Accuracy of Acetabular Component Positioning with a Fluoroscopically Referenced CAOs System, Computer Aided Surgery, Sep. /Nov. 2005; 10(5/6): pp. 321-327.

Stiehl et al., Validation and Metrology in CAOS, Part 1—Computer Assisted Orthopaedic Surgery, extracted on Dec. 9, 2006, Chapter 9, pp. 68-78.

Nogler M. Navigated Minimally Invasive Total Hip Arthroplasty. Surg Tech. Int. 2004; 12: 259-262.

Lewinnek GE, Lewis JL, Tarr R, Compere CL, Zimmerman JR. Dislocations after Total Hip-Replacement Arthroplasties. J of Bone and Joint Surg Am 1978; 60:217-220.

Stindel E, Gil D, Briard JL, Merloz P; Dubrana F, Lefevre C, Detection of the Center attic Hip Joint in Computer Assisted Surgery: an Evolution Study of the Surgetic Algorithm. Computer Aided Surgery 2005; 10: 133-139.

Sarin VK, Pratt WR, Bradley GW. Accurate Femur Repositioning is Critical During Intraoperative Total Hip Arthroplasty Leg Length and Offset Measurement. J Arthroplasty 2005; 20:887-891.

Widmer KH, Zurfluh B. Compliant Positioning of Total Hip Components. J Orthop Res 2004; 22: 815-821.

D' Lima DD, Urquhart AG, Buchler KO, Walker RH, Colwell CW. The Effect of Orientation of the Acetabular and Femoral Coinponent on the Range of Motion of the Hip Joint at Different-Head Neck Ratios. J Bone and Joint Surg 2000; 82: 315-321.

Della Valle AG, Padgett DE, Salvati EA. Preoperative Planning for Primary Total Hip Arthroplasty. J American Academy of Orthopaedic Surgeons 2005; 13: 455-462.

Soong M, Rubash HE, Macaulay W. Dislocation After Total Hip Arthroplasty. J American Academy of Orthopaedic Surgeons 2004; 12: 314-321.

Barrack RL. Dislocation After Total Hip Arthroplasty: Implant Design and Orientation. J American Academy of Orthopaedic Surgeons 2003; 11: 89-99.

Clark CR, Huddleston HD, Schoch EP, Thomas BJ. Leg- Length Discrepancy after Total Hip Arthroplasty. J American Acadeny of Orthopaedic Surgeons 2006; 14: 38-45.

Lazovic D., Cup and Stem Navigation with the Orthopilot System, in Navigation and MIS in Orthopaedic Surgery, ed. Stiehl JB, Konermann WH, Haaker RG, Digioia AM, Springer Medizin Verlag, New York, 2006, pp. 372-378.

Perlick L., Kalteis T., Tingart M., Bathis H., Luring C., Cup and Stem Navigated with the Vector Vision System, in Navigation and MIS in Orthopaedic Surgery, ed. Stiehl JB, Konermann WH, Haaker RG, Digioia AM, Springer Medizin Verlag, New York, 2006, pp. 378-384.

Duwelius PJ, Dorr LD, Minimally Invasive Total Hip Arthorplasty: An Overview of the Results, AAOS Instructional Course Lecture 57, 2008, pp. 215-222.

Wixson RL, Computer Assisted Total Hip Navigation, AAOS Instructional Course Lecture 2008, 57: 707-720.

Schmerwitz U, Total Hip Arthroplasty : First Experience with Pinless THA Software to Determine Leg Length and Offset, Orthopaedics 2007, 30: S124-126.

Extended European Search Report in PCT/US2008/012970 dated Oct. 22, 2014. 9 pages.

* cited by examiner

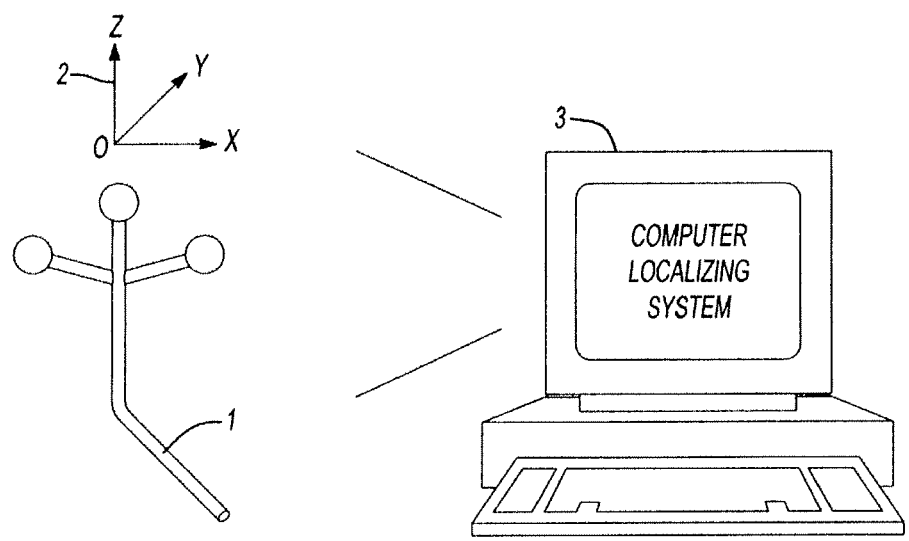
Fig-1
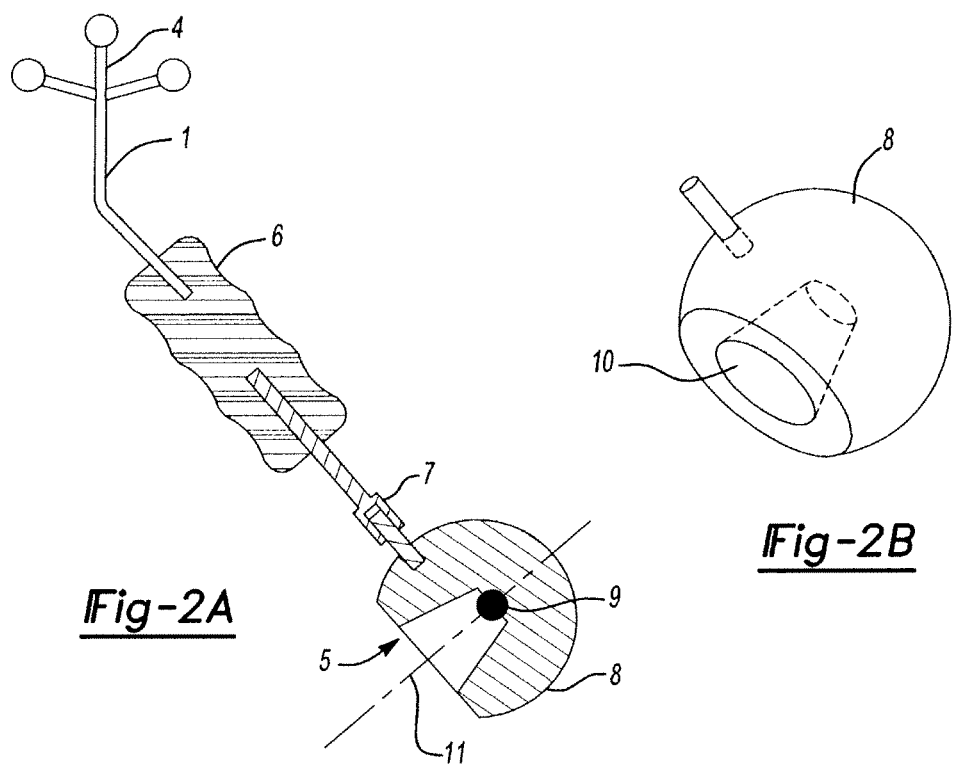
Fig-2A
Fig-2B

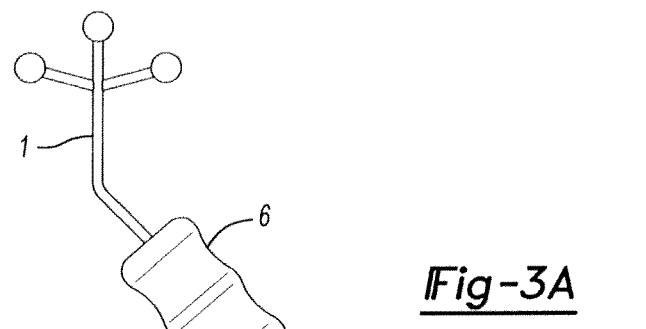
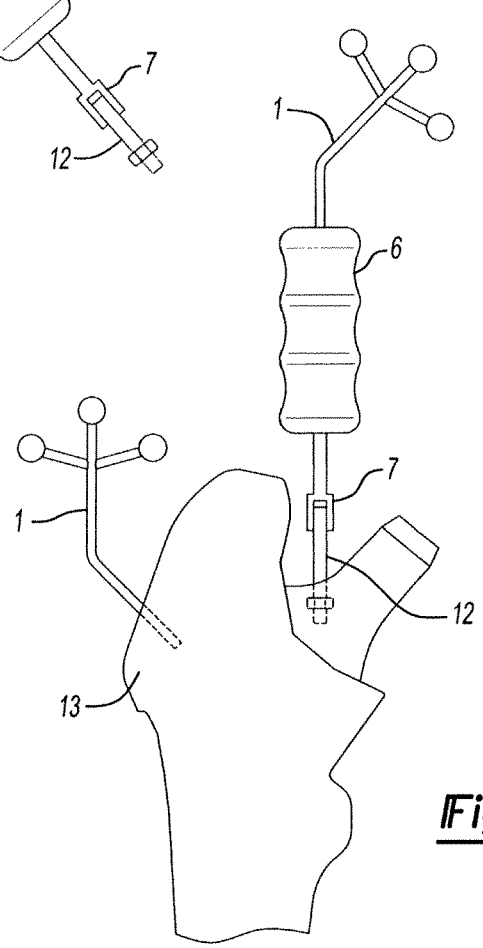

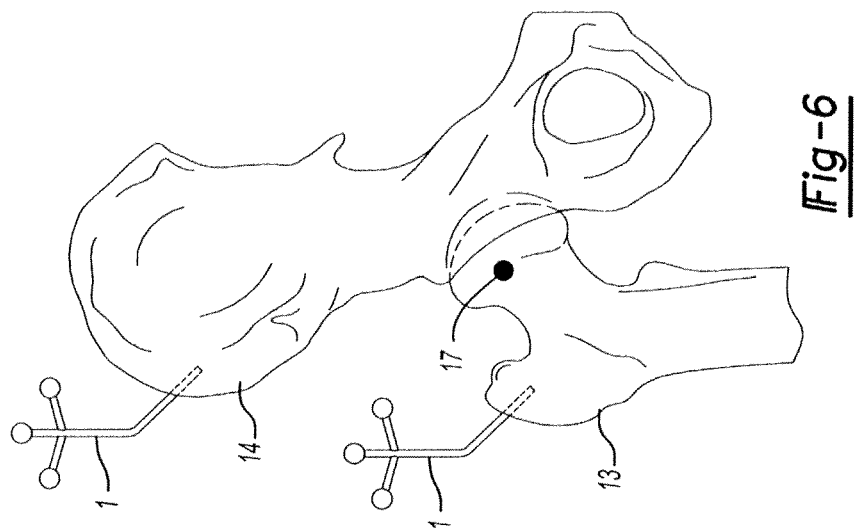
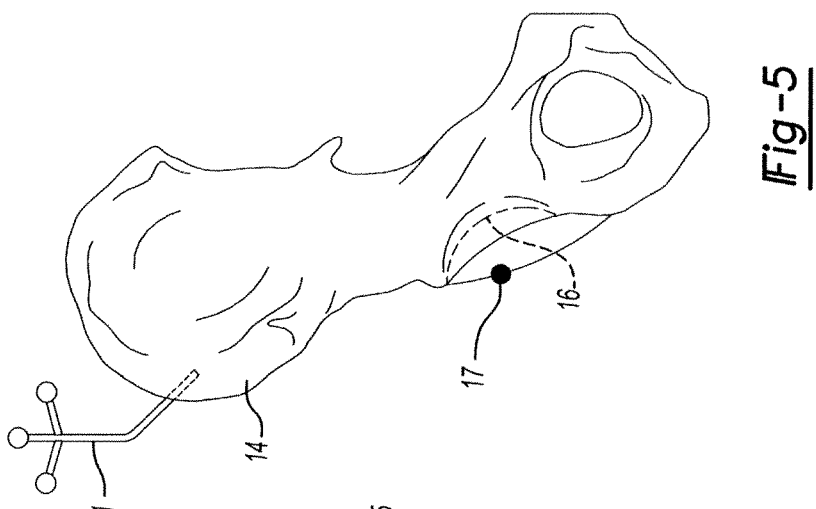
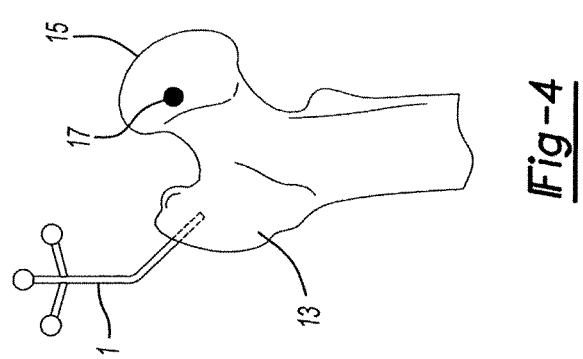

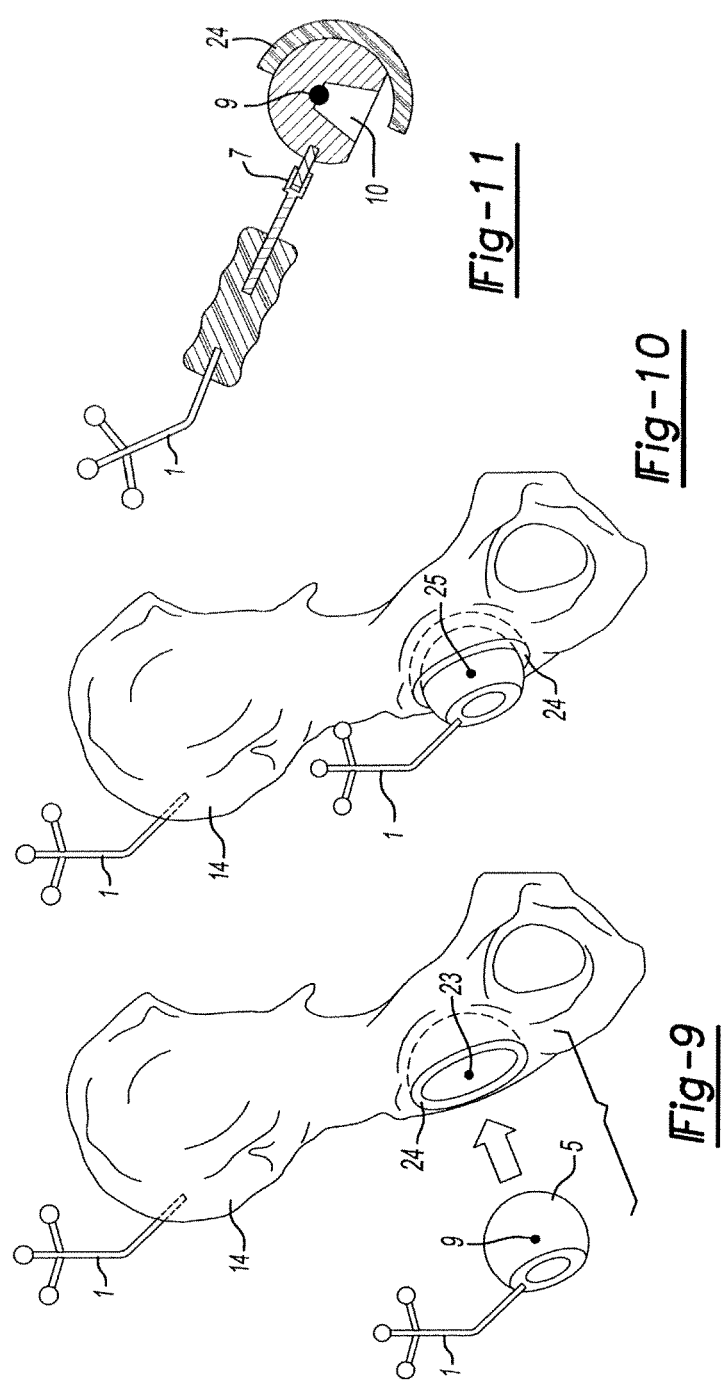

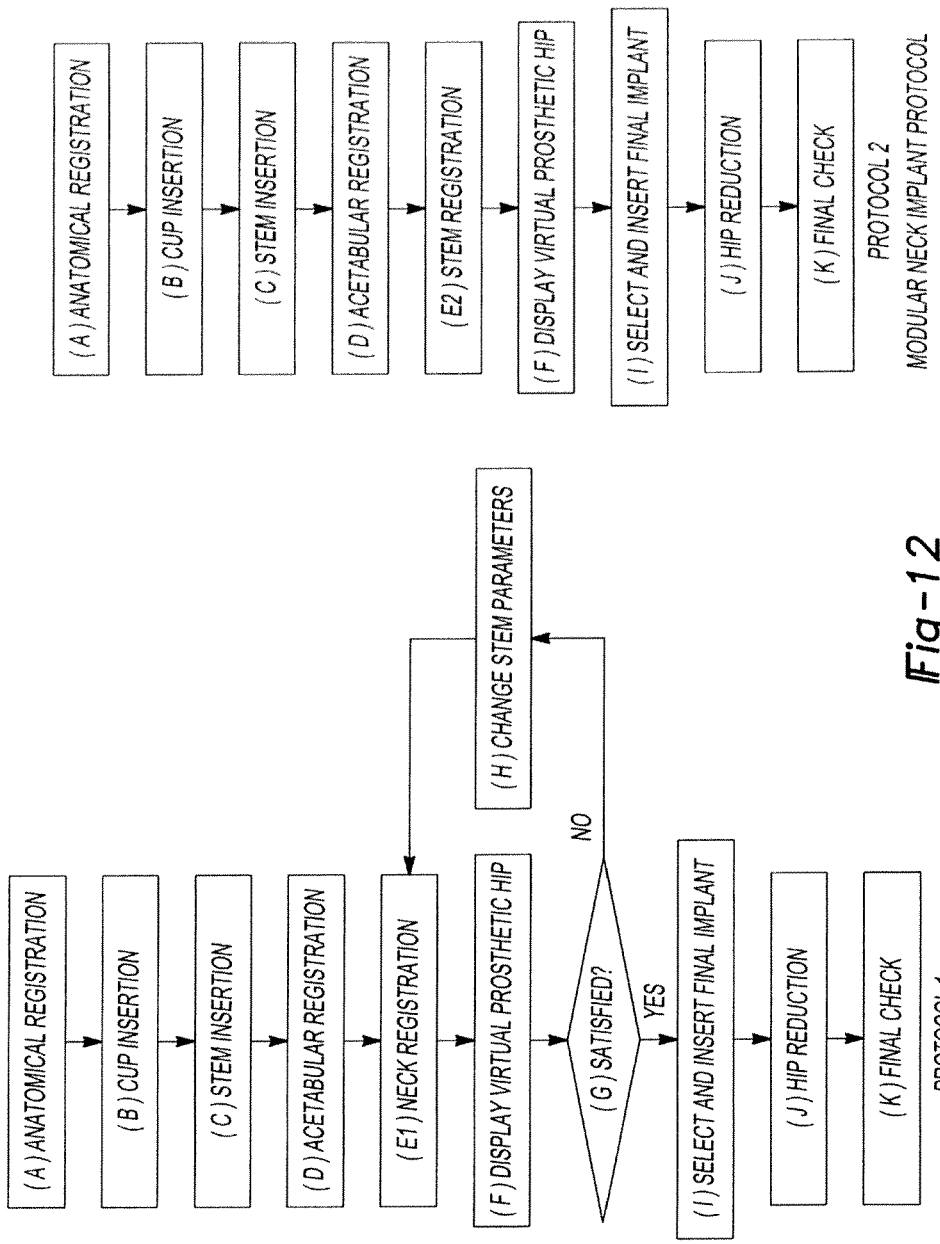

HIP IMPLANT REGISTRATION IN COMPUTER ASSISTED SURGERY

This is a non-provisional application claiming the benefit of U.S. Provisional Application No. 60/989,103, filed Nov. 19, 2007, and International Application Number PCT/US2008/012970, filed Nov. 19, 2008.

RELATED APPLICATIONS

This application claims priority from U.S. provisional utility application 60/989,103 filed Nov. 19, 2007 by the present inventor, entitled "Hip Implant Registration in Computer Assisted Surgery", the entire contents of which are expressly incorporated herein by reference and relied-upon.

TECHNICAL FIELD

The present invention relates generally to a system and method for computer-assisted Surgery (CAS), particularly in Total Hip Arthroplasty

BACKGROUND

It is known in the art to replace a natural hip joint with an artificial hip cup and stem replacement. Numerous artificial implants are available that can be installed to replace the natural joint with an artificial ball and socket combination. The medullary canal may be opened using a reamer to create a passage through the medullary canal in the upper end of the femur where a hip stem may be implanted. A stem or femoral component of an artificial implant is inserted into the reamed portion of the medullary canal in a secure seated position. Typically, femoral implants include a neck member that extends outward and away from the stem and terminates in a spherical knob for insertion into the acetabular implant of the hip in rotational contact throughout the three major orthogonal axes. The acetabular socket implants consist of a bowl or cup shaped device that is secured to the matching cup shaped dimension of the hip joint acetabulum.

Component malposition of the artificial implants has been recognized as an important source of problems or complications including fixation failure, limb length discrepancy, excessive wear, and dislocations. Dislocations may be related to component orientation, soft-tissue tension, or failure to restore hip biomechanics. [21, 22] Many of these factors are under the control of the surgeon. Ideally, the surgical intervention should reestablish the center of the hip joint to the anatomical center which typically will be the concentric center of the acetabulum. For certain reasons, the surgeon may desire to medialize this center or move the centrum to a more superior and medial non-anatomical position. Placement of the femoral component requires insertion of the body or stem of the implant into the medullary canal of the femur. The positional aspects of insertion relate to alterations of leg length and the amount of offset of the new artificial center of the femur compared to the original anatomical position. [12]

Change in leg length of the lower extremity can be determined by measuring: 1) the change of the artificial acetabular center from the normal anatomical center; and 2) the change of the artificial femoral center from the normal anatomical center. [24] The arthritic disease process with loss of the normal articular cartilage surfaces may diminish the leg length from normal. The surgeon then has several reasons to optimize leg length which includes restoring the leg to normal and to restore the length to match the contralateral leg. The femoral offset is the measure of distance from the anatomical center of the hip to an arbitrary position of the proximal femur such as the tip of the greater trochanter or a radiographic line that is centered on the anatomical axis of the proximal femoral shaft. [20] The femoral offset is increased during the operative intervention if the distance from the femoral center to the lateral reference is increased. Conversely, offset is diminished if the distance is decreased. The surgeon may desire to restore the offset that is determined to be normal or anatomical as this may best restore the normal functional muscle and soft tissue length. Biomechanical reasons may also lead to increasing the offset, as the lever arm for hip abduction may be made more favorable with this increase.

Another aspect of correct component position is the risk for component dislocation or disarticulation. This risk can be increased by malposition of the implants. [17] Adequate soft tissue tension is needed to keep the components in position and this will be decreased if the offset is inadequate. Positioning of both the acetabular and femoral components is another important factor determining stability. Excessive anteversion or retroversion of the acetabular component can lead to instability. Optimally, this position should be at about 40° of inclination from the transverse plane and 15° anteversion from the sagittal plane. One study demonstrated a four-fold increase in the potential for prosthetic dislocation if the position exceeded 10° from these optimal locations. [10] Another problem for acetabular position is the relationship of the pelvis to the longitudinal body plane. This also will affect the ultimate stability of the component by altering the acetabular component position. Femoral component version is less well understood but it has been recognized that adverse anteversion of both the cup and stem can lead to instability. With standard implant insertion through the conventional surgical approach, trial and final reduction or rearticulating of the prosthetic implants requires the surgeon or the assistant to manually distract the lower extremity to the extent that the devices are manipulated to the normal position. If this position is too long or too short, the final prosthetic position will to too tight or too loose, requiring adjustment. Adjustments could include driving the femoral prosthesis into the femoral intramedullary canal or placing a larger prosthesis that will tend to add length as the prosthesis cannot be advanced as far. This fitting process can become cumbersome, and an optimal scenario would include the use of a system that precisely determines the prosthetic position. [19] Approaching such precision would, therefore, tend to minimize the conventional 'trial and error' method of repeated prosthetic reductions.

Another innovation has been to substantially diminish the surgical exposure through a limited or minimally invasive approach. This evolutionary method decreases damage to the local tissues, decreases blood loss, and expedites patient recovery. [16] The method is more exacting because less anatomical structures are violated, at the expense of limited access of certain landmarks. The surgeon has more difficulty recognizing structures that guide typical bone resection. Computer assisted surgery (CAS) or navigation has emerged as a new method that will give the surgeon intraoperative positional information to improve component position. For minimally invasive surgery, the CAS system may enhance the understanding of the normal anatomy and allow precise direct placement of trial implants, minimizing the 'trial and error' method of optimizing prosthetic placement. [9] The basic components of a CAS system are the computer which will record and integrate three dimensional position data; a positional data gathering tool which could be optical, ultrasound, electromagnetic, or radio frequency; and the targeted rigid bodies that are defined to the computer by a referencing protocol. Dynamic rigid bodies may be a human anatomical structure, a surgical instrument, a joint prosthesis, or a positional marker. These rigid bodies are then portrayed in a 'virtual' three dimensional computer representation where the surgeon may readily understand the positional inter-relationships.

CAS of the hip joint for prosthetic arthroplasty initiated with methods that delineate the anterior plane of the pelvis.[18] The anterior pelvic plane is in the coronal plane of the human body and connects the points of the two anterior superior iliac spines and the pubic tubercles. This plane then describes an x-y-z axis that allows the computer to measure various points about the pelvis, such as the anatomical hip center, the acetabular center, the femoral center, femoral offset and the leg length. The first important application in orthopaedic surgery was using this framework to enable guidance of acetabular component insertion where the surgeon could monitor in real time the inclination and anteversion of acetabular prosthetic positioning. Various methods have been developed to measure and describe the anatomical points used by the surgeon. The hip femoral pivot method uses a referenced femur, which when moved in a circular fashion, will define the focus of the cone shaped movements as the anatomical hip center.[11] Another method allows the surgeon to use digital radiographs or images where the surgeon picks the anatomical center by assessing the center of the acetabulum and femoral head. A third method, the least squares method, picks the instant center based on a series of reference points that describe the floor of the acetabulum. Recent CAS systems have navigated femoral position in relation to the pelvic reference by establishing a point of reference on the proximal femur and then monitoring this position during the surgical procedure. Typical outputs may include leg length measure, femoral offset measure, and femoral stem anteversion measure. However, most recent CAS systems can only measure the beginning and final positions of the femur in relation to the pelvis and do not eliminate the 'trial and error' method of placing the implants and doing reductions to assess the effects of this positioning.[14, 15] Thus, methods of minimally invasive surgery (MIS) would welcome further advantages of improved CAS techniques in measuring anatomical and prosthetic objects.[13]

A device and a method for implanting artificial joint components are known from U.S. Pat. No. 5,995,738. This Digioia patent creates an artificial component model that allows three dimensional simulation of limb range of motion of the femur and acetabulum driving the surgical procedure. Based on this patient specific determination, the acetabulum component can then be guided to the resolved "optimal position". The computer assisted surgical system used to track references fixed to patient bones and surgical instruments is described in greater detail in commonly assigned U.S. Pat. No. 6,315,659. That patent describes the ability of the CAS system to render the momentary positional data of the patient and that of surgical instruments and apparatus employed in the operation, visibly on the display terminal of the computer. It is known that some devices exist to measure intraoperatively stem position.[1, 4, 6] It is known that some devices exist to measure intraoperatively acetabular component position.[1, 2, 3, 5] It is known that some devices exist to measure both stem and acetabular relative positions when the hip is anatomically reduced.[1, 6] The Grimes patent registers the anatomical dimensions of the implants for image guided implant insertion.[8]

Prior approaches have not sought to directly measure the position of the femur and acetabulum independently of each other and based upon a unifying reference point which, in the case of the present invention, is the anatomical hip center.

Neither have others sought a single device to measure both stem and cup position, which offers the advantage of simplifying the ergonomics.

Nor have others sought a device intended to be used when the hip is dislocated, which would offer the advantage of accelerating the decision process, by avoiding reducing the hip to measure prosthesis implant positions then dislocating the hip to change the implant type if necessary.

SUMMARY OF THE INVENTION, OBJECTS AND ADVANTAGES

According to an aspect of the present invention there is provided a computer assisted surgical navigation system for registering the position of prosthetic hip joint components. The system includes a first reference element applied to the pelvis that generates a first three-dimensional dynamic reference body, which is independently registered in the system. A second reference element is applied to the femur that generates a second three-dimensional dynamic reference body, which is independently registered in the system. A three-dimensional dynamic reference point derived from the first and second dynamic arrays represents the native anatomical center, which is independently registered in the system A tracking device generates a third three-dimensional dynamic reference array, which is independently registered in the system. The device has a pre-determined shape and dimensions that precisely articulate with an acetabular component. The device has a further shape and dimensions that independently articulate precisely with a neck portion of a femoral component, representing a prosthetic joint center independently registered in the system. The tracking device concurrently registers in the system the three dimensional positions of the femoral and acetabular prosthetic components, the prosthetic joint center and the native anatomical joint center, respectively. This enables the surgical team to intraoperatively represent alterations in three dimensional location of the leg length and offset prior to any reduction of the prosthetic joint. In a preferred embodiment, there is an optical camera registered in the system for tracking the device. In another preferred embodiment, the tracking device is a hemispherical ball having a pre-determined geometry and dimensions, which precisely articulate with the acetabular component. In yet another preferred embodiment, the tracking device is a hemispherical ball having a further pre-determined geometry and dimensions, which precisely articulate with the neck, more preferably with a modular neck and also more preferably via a slot in the ball that receives a trunion from the neck. In still another preferred embodiment, the reference elements each have individualized arrangements of optical markers. In still a further preferred embodiment, the tracking device may be attached to a trial implant or broach instrument, or to a primary implantable femoral component. More preferably, any of the trial and broach instruments and primary implant may be modular.

According to an aspect of the present invention there is provided a computer assisted surgical navigation system for registering the position of prosthetic hip joint components. The system includes a first reference element applied to the pelvis that generates a first three-dimensional dynamic reference array, which is independently registered in the system. A second reference element is applied to the femur that generates a second three-dimensional dynamic reference array, which is independently registered in the system. A three-dimensional dynamic reference point is derived from the first and second dynamic arrays and represents the native anatomical center, which is independently registered in the system. A third three-dimensional dynamic reference point represents the native anatomical center, which is derived from the first and second dynamic arrays and independently registered in the system. A tracking device generates a third three-dimensional dynamic reference array, which is independently registered in the system. The device has a pre-determined hemispherical ball shape and dimensions that precisely articulate with an acetabular component. The device has a further pre-determined shape and dimensions that independently and precisely articulate with a modular neck of a femoral component, representing a prosthetic joint center that is independently registered in the system. The tracking device concurrently registers in the system the three dimensional positions of the femoral and acetabular prosthetic components, the prosthetic joint center and the native anatomical joint center, respectively. This enables the surgical team to intraoperatively represent alterations in three dimensional location of the leg length and offset prior to any reduction of the prosthetic joint.

According to another aspect of the present invention there is provided a method for registering the position of prosthetic hip joint components during a total joint arthroplasty procedure. The method provides a computer assisted three-dimensional surgical navigation system. The method includes the step of applying a first reference element to the pelvis, generating a first three-dimensional dynamic reference array and independently registering the first array in the system. Another step is applying a second reference element to the femur, generating a second three-dimensional dynamic reference array and independently registering the second array in the system. A three-dimensional dynamic reference point is derived from the first and second dynamic arrays and represents the native anatomical center, which is independently registered in the system. The method provides a tracking device with a pre-determined shape and dimensions, generating a third three-dimensional dynamic reference array representing the device and independently registering it in the system. The method precisely articulates the device independently with a correspondingly shaped and sized acetabular cup component and a neck portion of a femoral component, representing a prosthetic joint center and independently registering it in the system. The method concurrently registers the three-dimensional positions of the femoral and acetabular components, the prosthetic joint center and the native anatomical joint center, respectively, in the system. This method enables the surgical team to intraoperatively represent alterations in three dimensional location of the leg length and offset in the system, prior to any reduction of the prosthetic joint.

In a preferred embodiment, the method includes the step of tracking the device using an optical camera registered in the system and, more preferably, providing the first and second reference elements with individualized arrangements of optical markers. Another preferred step is providing the device with a hemispherical ball shape having pre-determined dimensions and precisely articulating the ball with the acetabular cup component. Yet another preferred method step is providing the device with a hemispherical ball shape having pre-determined dimensions and precisely articulating the ball with the neck of the femoral component, more preferably, the femoral component is provided with a modular neck. Also more preferred is the method step of providing the ball with a slot that engages a trunion on the neck of the femoral prosthesis. In yet a further preferred embodiment. In still a further preferred embodiment, the tracking device may be attached to a trial implant or broach instrument, or to a primary implantable femoral component. More preferably, any of the trial and broach instruments and primary implant may be modular.

According to a preferred embodiment, a computer assisted surgical navigation system is provided for registering the position of prosthetic hip joint components. An optical reader or camera is registered in the system. A first reference element is applied to the pelvis including an individualized arrangement of optical markers that generates a first three-dimensional dynamic reference array, which is independently registered in the system. A second reference element is applied to the femur including another individualized arrangement of optical markers that generates a second three-dimensional dynamic reference array, which is independently registered in the system. A three-dimensional dynamic reference point is derived from the first and second dynamic arrays and represents the native anatomical center, which is independently registered in the system. A tracking device discernable by the camera or reader generates a third three-dimensional dynamic reference array, which is independently registered in the system. The device has a pre-determined hemispherical shape and dimensions that precisely articulate with an acetabular cup component. The device independently has a further geometry and dimension that precisely articulate with a neck of a femoral component to represent a prosthetic joint center, which is independently registered in the system. The tracking device concurrently registers the three dimensional positions of the femoral and acetabular components, the prosthetic joint center and the native anatomical joint center, respectively, in the system. This enables the surgical team to intraoperatively represent alterations in three dimensional location of the leg length and offset prior to any reduction of the prosthetic joint. In a preferred embodiment, the system is provided with a femoral component that is a trial instrument or broach adapted for precisely articulating with the tracking device.

It is an object of the present invention to enable minimally invasive methods by providing a measuring device that can be engaged with the prosthetic targets through a limited surgical approach. That is, the present invention creates a reference tool that allows the surgeon to position the hip prosthetic implants using the computer to predict the final prosthetic position in relation to the various anatomical and 'virtual' points.

An advantage of the present CAS system is that the positions of the anatomical features are established in a three dimensional model, prior to any surgical manipulations such as cutting the bone of the proximal femur. More advantageously, with this information the preliminary prosthetic sizing options may be rendered by the computer. By directly measuring the prosthetic hip center of the two components (the femoral head and the acetabular cup) independently of each other, the surgeon can actually make changes or improvements in the final position.

Another advantage of the present invention is a system that will eliminate or reduce the time needed for performing the empirical trial reductions to assess implant position and soft tissue tension. That is, a surgery that is quicker, cheaper and less complex. By improving the precision of leg alignment and ligament balancing, two of the most important factors determining long term outcome are affected.

Yet another advantage is a reference tool to gauge whether the surgeon has changed the center position of the hip joint in preparation of the anatomical acetabulum and proximal femur for accepting the prosthetic components—without reduction of the joint.

The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

BRIEF DESCRIPTION

FIG. 1 is an elevational view of a preferred reference element with optical markers, representing its three-dimensional dynamic reference array in the navigation system of the present invention;

FIG. 2A is a sectional view of a reference element of FIG. 1 assembled with the tracking device shown as a hemispherical ball with a trunion hole and a handle for surgical manipulation, to register the device in the surgical navigation system according to the present invention; and FIG. 2B is a partial perspective view of FIG. 2A;

FIG. 3A is a sequential view of FIG. 1, assembled with a handle similar to FIG. 2A with the tracking device shown as the preferred hemispherical ball with a trunion hole and a handle for surgical manipulation to register the device in the surgical navigation system (and as placed in the neck per FIG. 3B), according to the present invention;

FIG. 3B is sequential view of FIG. 1, assembled with a handle similar to FIG. 2A, with the tracking device fixed to the prosthetic femoral component body, to register this device in the surgical navigation system without the presence of the femoral neck;

FIG. 4 is an elevational view of the native anatomical femur shown with a reference element similar to that shown in FIG. 1 according to the invention, and further indicating the center of the femoral head;

FIG. 5 is an elevational view of the native anatomical pelvis shown with a reference element similar to that shown in FIG. 4 according to the present invention, which further depicts the center of the acetabulum;

FIG. 6 is a sequential view of FIG. 5 showing the native anatomical hip joint articulated (together with reference elements applied to the femur and pelvis per FIG. 4 for registration in the navigation system according to the present invention), indicating the center of the native hip joint;

FIG. 9 is an exploded view showing the articulation of the preferred tracking ball indicating the center of the preferred tracking ball be placed (large arrow) to match the center of the articular cup component;

FIG. 10 is a sequential view of FIG. 9 showing the preferred tracking ball articulated with the acetabular cup component registering the precisely known center of the prosthetic joint according to the present invention;

FIG. 11 is a partial sectional view of FIG. 10 showing the articulated prosthetic hip joint components; and FIG. 12 is a surgical procedure flow diagram, showing a Protocol 1 for femoral components having a non-modular neck, and a Protocol 2 for a modular neck.

DETAILED DESCRIPTION

Introduction to Computer Navigation and Trackers

The present invention is used in combination with a Computer Assisted Surgical (CAS) System. The localization principle of the CAS system may be based on optic, magnetic, radio-frequency, ultrasound measurement technologies or articulated passive or robotic arms.

Tracker Description

Figure 7:
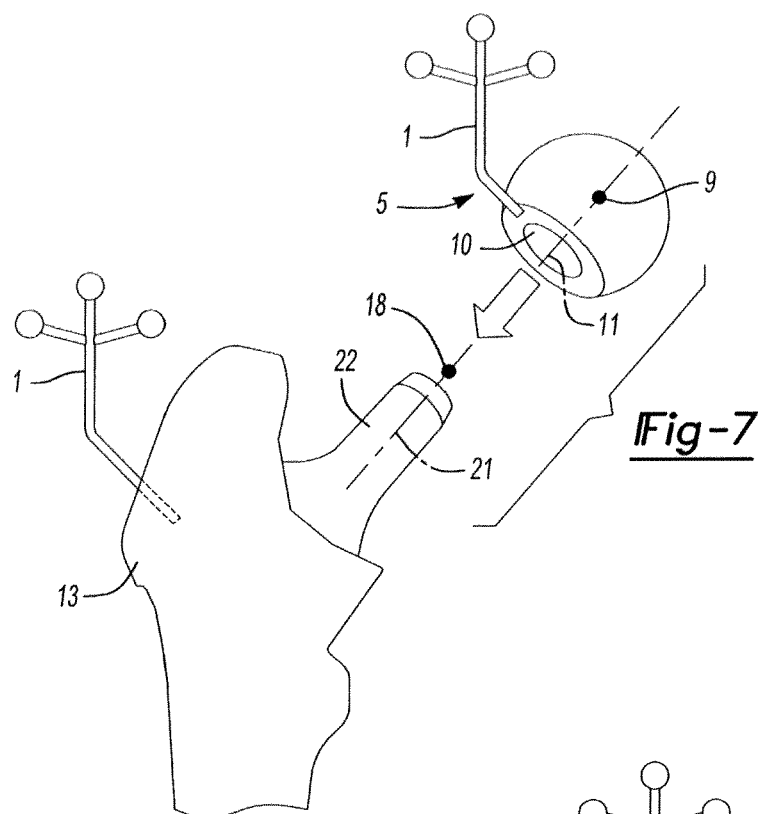
FIG. 7 is an exploded view showing articulation of the preferred tracking ball with the neck of the femoral component along an axis of the neck (large arrow), indicating the precisely known center of the ball relative to the neck size and dimensions as contemplated by the present invention.
Figure 8:
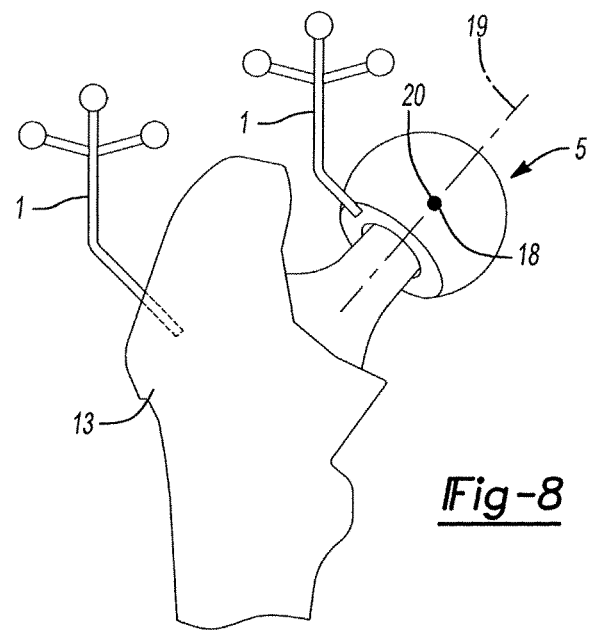
FIG. 8 is a sequential view of FIG. 7 showing insertion of the preferred tracking ball onto the neck of a femoral component along an axis (large arrow), indicating the precisely known center of the ball relative to the neck size and dimensions contemplated by the present invention.

Referring to FIGS. 1-12, a tracker 1 is a device that is localized by the localizer system 3 of the CAS system. For each tracker is defined a unique coordinate system (O, X, Y, Z) 2, also called a reference. One tracker is fixed on the femur 13 (FIG. 4), one on the pelvis 14 (FIG. 5), and one on the Device 5 (FIG. 2). By measuring those trackers in real-time, the localizer system provides the relative position of the femoral reference, the pelvis reference, and the Device reference during the surgical procedure. For convenience purpose, the tracker is represented in all figures by 3 branches device with 3 spherical balls, as it looks like for an optical passive wireless tracker like standard Spectra camera from Northern Digital Inc. (Ontario, Canada), even if the tracker technology may be not optical, but magnetic, ultrasounds, radio-frequency, or robotics.

Tracking Software

A reference 4 is also attached to the localizer system 3. For each tracker 1 detected by the localizer system 3, the localizer system 3 gives the transformation matrix, composed of 3 translations and 3 rotations, between the localizer reference 4 and the tracker reference 2. As an example, if $MF_i$ is the matrix between the localizer reference and the femoral reference, and if $MD_i$ is the matrix between the localizer reference and the Device reference, then the relative position $M_i$ between the Device reference and the femoral reference is $M_i = MD_i - 1 \cdot MF_i$. With this method one can express every geometrical data (point, line, shapes) that are known in a given reference into another reference. As an example, if C is the 3D point corresponding to the ball center 9 expressed by its coordinates (x, y, z) in the Device reference, and if C' is the 3D point corresponding to the ball center 9 in the femoral reference, expressed by (x', y', z'), then $C' = Mj \cdot C$. This typical workflow for transferring geometrical from one reference to another is described in FIG. 12.

Device Description

The Device, described in FIG. 2, is composed of a tracker 5 to allow the CAS system to track the whole Device. The tracker is mounted on a handle 6. The handle helps the operator manipulating the Device. A reproducible fixation system 7 allows the operator to assemble and disassemble easily the ball 8 during the surgical procedure. The ball contains a tapered trunion hole 10 that fits with femoral necks. The geometry of the Device is perfectly known, meaning that the coordinate of the trunion hole axis 11, and the ball center 10 are perfectly known in the tracker reference 5.

Tracker Fixation Description

Preferably, the tracker fixation 7 allows the operator to assemble and disassemble the tracker easily from the ball. One may provide the operator with several ball types, such as different combinations of diameters and trunion hole shapes, which implies that the operator changes the ball before or during the surgery. The fixation is reproducible and the components geometry is perfectly known, so that once the ball is attached to the tracker, the ball position is known in the tracker reference. Preferably, the fixation is manipulated without any tool such as screwdriver. Optionally, the tracker fixation can be fixed and rigid, with no possibility to disassemble the ball.

Femoral Neck Registration

For a large majority of hip implants, the top part of the prosthetic femoral neck (FIG. 7) 22 can be modeled by a cone, with a revolution axis, called the neck axis 21. In addition, there are few cone types, in order to allow a cup and head manufacturer to be compatible with other manufacturer's stems. The invention is best used with the cones that are standardized, which represents a very large proportion of the market, or it is necessary to know the specific geometry of cones for other cases. The trunion hole 10 is designed to fit with a total hip prosthetic femoral neck so that there is a unique reproducible position of the ball with respect to the femoral neck, except around the neck axis. Once in position (FIG. 8), the trunion hole axis 11 and the neck axis 21 are coincident 19, and the ball center 9 corresponds to the future prosthetic head center 18,20. The inner trunion hole is positioned with respect to the ball center such that once it is placed on the neck, the ball center corresponds to a "Head neck 0" of the most common implants. The "Head Neck 0" is always defined by implant manufacturers as the default neck. Other heads are proposed by implant manufacturers with an offset along the neck axis, such as "Head Neck +2mm", "Head Neck −2mm", etc. Optionally, if the ball center does not correspond to the "neck 0" of a given implant, one may enter in the CAS system the offset value between the ball center and the "head neck 0" of the implant. By default, this offset value is 0. Thanks to the trackers that give the position of the Device reference with respect to the femoral reference, one may deduce the prosthetic neck axis 21 and the prosthetic head center 18 in the femoral reference. The trunion hole authorizes the ball to be assembled and disassembled easily from the femoral neck, allowing the operator to remove the ball, change the prosthetic parameters such as the neck axis or neck length, and redo the measurement with the ball. The software workflow that computes the femoral head center 18 position with the help of the Device is described in FIG. 12. The software workflow that computes the femoral neck axis 21 position with the help of the Device is similar to the one presented FIG. 12 by changing the geometrical data, i.e. replacing the head center 18 of the neck axis 21.

Acetabular Registration

The external shape of the ball 8 is designed so that it precisely articulates with the desired dimension of the acetabular component 24. The external shape is partially spherical, at least one fourth of a sphere, but preferably one half sphere, in order to fit well with the acetabular component 24 (FIG. 9). There is a unique and reproducible position in translation of the ball with respect to the acetabular component. That means that once the ball is placed inside the acetabular component (FIG. 10), the acetabular center 23 and the ball center 9 are coincident 25. Thanks to the trackers that give the position of the Device reference with respect to the pelvic reference, one may deduce the acetabular center in the pelvic reference. The external shape authorizes the ball to be assembled and disassembled easily from the acetabular component, allowing the operator to remove the ball, change the prosthetic parameters, and redo the measurement with the ball. The software workflow that computes the acetabular center 23 position with the help of the Device is similar to the one presented FIG. 12, except the Device is positioned in the acetabular component instead of the femoral neck, and the femoral reference is replaced by the pelvic reference.

Anatomical Registration

There are several solutions to perform the anatomical registration of the hip joint parameters at the beginning of surgery. Preferably, the anatomical center of the hip joint is determined with a kinematic reference method (solution 1) where the center can be defined by movement of the femoral reference in a circular fashion also known as pivoting. As the hip joint is fixed in the pelvic reference, movement of the femoral reference describes a cone of movement, the center of which is the center of the joint 17 (FIG. 6). In this case, the Device helps comparing the prosthetic hip center to the anatomical hip center. Optionally, the anatomical center of the hip is computed separately on the femur and the pelvis (solution 2). On the femoral side, one may acquire the femoral head surface its most spherical part with a dedicated pointer reference, in order to reconstruct the sphere passing best by the points collected with the pointer using a least-squares method, and compute the anatomical femoral head center of the center of the reconstructed sphere 15 (FIG. 4). On the acetabular side, one may acquire the acetabular surface with a dedicated pointer reference in a similar way, by calculating the least-squares sphere that fits with the points collected in non worn parts of the anatomical acetabulum, in order to compute the anatomical acetabular center 16 (FIG. 5). In this case, the Device helps comparing the prosthetic acetabular and femoral centers respectively to the acetabular and femoral hip centers. Optionally, one may simply compute the femoral position with respect to the pelvis position (solution 3). In this case, the Device helps comparing the prosthetic position with respect to the anatomical position of the lower limb, without any indication on the anatomical and prosthetic hip centers.

Protocol Description

Preferably, the surgical Protocols 1 and 2 using the Device are described FIG. 12. The Protocol 1 particularly fits with the non-modular neck implants, where the implants are not in the CAS database, because this protocol is universal and highly independent of the implant. In this protocol, the operator registers the acetabular component (D) position and the femoral neck (E1) position. Then, the CAS system displays on the screen the virtual prosthetic hip (F) in relation with the anatomical measurements. This step allows the surgeon to visualize the simulation of the hip parameters without reduction of the hip joint, and change accordingly the neck length in order to restore a correct leg length and lateral offset for best hip stability. If the surgeon is still not satisfied of the prosthesis positions (G), he may change the implant stem parameters (H) such as position, orientation, or chose a stem with different characteristics such as lateralization or inclination, and then redo the neck registration with the Device (E1).

The Protocol 2 particularly fits with modular neck implants where the implant database is known by the CAS system. In this protocol, the operator registers the acetabular component position (D) and the stem (E2) position. Then, the CAS system displays the virtual prosthetic hip like in the previous protocol (F). As the CAS system knows the implant database, it may allow the surgeon to change virtually not only the neck length like in the Protocol 1, but also the neck type. It is a significant advantage if one considers that a modular neck implant may offer more than one hundred of possibilities. By simulating virtually the neck type using the touch screen of the CAS system, the operator does not need to change actually the implants and redo the measurement like in the Protocol 1.

For both protocols, if the anatomical registration has recorded a hip center, by Solution 1 or 2 described before, then the CAS system displays the offset between the prosthetic hip center and the anatomical hip center in the 3 projection plans (frontal, sagittal, axial), as well as the resulting position in terms of lengthening, lateral offset, and sagittal offset of the prosthetic lower limb compared to the anatomical situation.

For both protocols, once the virtual proposal is accepted, the operator selects and inserts final implants (I), reduces the hip (J) and makes a final check (K). Final check consists in measuring the final changes of leg length and offset of the hip joint in comparison with pre-operative measurements. Final check may also include registering the final prosthetic hip center, by a kinematic movement for instance, and display the comparison with the anatomical situation.

Optionally, the acetabular registration (D) is done just after the cup insertion (B) and the femoral neck registration (E1) or the stem registration (E2) is done just after the stem insertion (C).

Stem Registration

In some cases it is preferable to digitize the stem without any neck. This situation occurs with modular neck implants in particular. In those cases, we use an adaptor to the stem 12 (FIG. 3), instead of a trunion hole adaptor to the neck. The fixation system to the stem is the one used by the standard stem impactor, usually dependent of the implant type and brand. Most of stem fixation systems are female on the stem part, in order to avoid conflicting soft tissues once the stem impactor is removed, which leads to design in most cases a male fixation part on the Device 12. If the fixation part of the Device is female, there is a possibility to place the female part inside the ball (FIG. 11). Wherever the female part 10 is on the ball, except on the tracker fixation system 7, it does not conflict with the acetabular component 24 registration functionality. However, if the fixation part of the Device is male, one need to make sure that the male part does not conflict with the acetabular registration. If placing the male part on the ball surface is not convenient, one may optionally design a second tip 12 that is fixed to the handle 6, instead of the ball 8.

Device Manufacturing

The Device 12 may be manufactured from any suitable medical material, which would include stainless steel or plastic. The Device 12 may be embodied in other specific forms without departing from its spirit or essential characteristics. The described embodiment is to be considered in all respects only, as illustrative and not restrictive and the scope of the Device is, therefore, indicated by the appended claims rather than by the foregoing description. All changes which come within the meaning and range of equivalency of the claims are to be embraced within their scope.

CITATIONS

[1] USPA 2004/0097952
[2] USPA 2004/0254584
[3] USPA 2005/0203536
[4] U.S. Pat. No. 5,995,738
[5] USPA 2004/0143340
[6] U.S. Pat. No. 7,419,492
[7] U.S. Pat. No. 6,991,655
[8] U.S. Pat. No. 6,351,659
[9] Nogler M. Navigated minimally invasive total hip arthroplasty. Surg Tech. Int. 2004; 12: 259-262,
[10] Lewinnek G E, Lewis J L, Tarr R, Compere C L, Zimmerman J R. Dislocations after total hip-replacement. J Bone and Joint Surg Am 1978; 60: 217-220.
[11] Stindel E, Gil D, Briard J L, Merloz P, Dubrana F, LeFevre C. Detection of the center of the hip joint in computer assisted surgery: an evolution sutdy of the Surgetic algorithm. Computer Aided Surgery 2005; 10: 133-139.
[12] Sarin V K, Pratt W R, Bradley G W. Accurate femur repositioning is critical during intraoperative total hip arthroplasty leg length and offset measurement. J Arthroplasty 2005; 20: 887-891.
[13] Lazovic D. Cup and stem navigation with the Orthopilot System. In Navigation and MIS in Orthopaedic Surgery, ed. Stiehl J B, Konermann W H, Haaker R G, Digioia A M. Springer Medizin Verlag, Heidelberg, pp 372-378.
[14] Perlick L, Kalteis T, Tingart M, Bathis H, Luring C. Cup and stem navigated with the Vector Vision System. In Navigation and MIS in Orthopaedic Surgery, ed. Stiehl J B, Konermann W H, Haaker R G, Digioia A M. Springer Medizin Verlag, Heidelberg, pp. 378-384.
[15] Widmer K H, Zurfluh B. Compliant positioning of total hip components. J Orthop Res 2004; 22: 815-821.
[16] Duwelius P J, Dorr L D. Minimally invasive total hip arthorplasty: an overview of the results. AAOS Instructional Course Lecture 57: 215-222.
[17] D'Lima D D, Urquhart A G, Buchler K O, Walker R H, Colwell C W. The effect of oreintation of the acetabular and femoral component on the range of motion of the hip joint at different head-neck ratios. J Bone and Joint Surg 2000; 82: 315-321.
[18] Wixson R L. Computer assisted total hip navigation. AAOS Instructional Course Lecture 2008; 57: 707-720.
[19] Schmerwitz U. Total hip arthroplasty: first experience with pinless THA software to determine leg length and offset. Orthopaedics 2007; 30: S124-126.
[20] Della Valle A G, Padgett D E, Salvati E A. Preoperative planning for primary total hip arthorplasty. J American Academy of Orthopaedic Surgeons 2005; 13: 455-462.
[21] Soong M, Rubash H E, Macaulay W. Dislocation after total hip arthroplasty. J American Academy of Orthopaedic Surgeons 2004; 12: 314-321.
[22] Barrack R L. Dislocation after total hip arthroplasty: implant design and orientation. J American Academy of Orthopaedic Surgeons 2003; 11: 89-99.
[23] Clark C R, Huddleston H D, Schoch E P, Thomas B J. Leg-length discrepancy after total hip arthroplasty. J American Academy of Orthopaedic Surgeons 2006; 14: 38-45.

The invention claimed is:

1. A computer assisted surgical navigation system for registering the position of prosthetic hip joint components, the system comprising:
an acetabular prosthetic component;
a femoral prosthetic component;
a first reference element applied to the pelvis that generates a first three-dimensional dynamic reference array, which is independently registered in the system;
a second reference element applied to the femur that generates a second three-dimensional dynamic reference array, which is independently registered in the system;
a three-dimensional dynamic reference point representing the native anatomical center that is independently registered in the system and derived from the first and second dynamic arrays;
a tracking device that generates a third three-dimensional dynamic reference array, which is independently registered in the system, the device having a portion with a ball shape and dimensions that precisely articulate with the acetabular component and a female or a male part formed in or on said ball-shaped portion and having shape and dimensions that independently articulate precisely with a neck portion of the femoral component, representing a prosthetic joint center independently registered in the system, the geometry of said ball-shaped portion of the device being known with respect to the third three-dimensional dynamic reference array; and wherein the tracking device concurrently registers in the system the three dimensional positions of the femoral and acetabular prosthetic components, the prosthetic joint center and the native anatomical joint center, respectively, to intraoperatively represent alterations in three dimensional location of the leg length and offset prior to any reduction of the prosthetic joint.

2. The system of claim 1 further comprising an optical camera registered in the system for tracking the device.

3. The system of claim 2 wherein the reference elements each have individualized arrangements of optical markers.

4. The system of claim 1 wherein the tracking device is a hemispherical ball having a pre-determined geometry and dimensions, which precisely articulate with the acetabular component.

5. The system of claim 1 wherein the tracking device is a hemispherical ball having a further pre-determined geometry and dimensions, which precisely articulate with the neck portion of the femoral prosthesis.

6. The system of claim 1 wherein the tracking device has a further pre-determined geometry and dimensions, which precisely articulate with a modular neck of the femoral prosthesis.

7. The system of claim 1 wherein the tracking device has a further pre-determined geometry and dimension including a slot that precisely articulates with a trunion on the neck of the femoral prosthesis.

8. The system of claim 1 wherein the tracking device may be attached to a trial implant or rasp instrument, or to a primary implantable femoral component.

9. The system of claim 1 wherein the femoral component is a modular trial instrument or broach adapted for precisely articulating with the tracking device.

10. A computer assisted surgical navigation system for registering the position of prosthetic hip joint components, the system comprising:
an acetabular cup component;
a femoral prosthetic component;
a first reference element applied to the pelvis that generates a first three-dimensional dynamic reference array, which is independently registered in the system;
a second reference element applied to the femur that generates a second three-dimensional dynamic reference array, which is independently registered in the system;
a three-dimensional dynamic reference point representing the native anatomical center that is independently registered in the system and derived from the first and second dynamic arrays;
a tracking device having a handle and a hemispherical portion with a center, which generates a third three-dimensional dynamic reference array independently registered in the system, the hemispherical portion being attached to the handle and precisely articulating with the acetabular cup component such that the center of the hemispherical portion of the device and the center of the acetabular component are coincident, the hemispherical portion having a further pre-determined trunion hole portion distant from the handle that independently and precisely articulates with a modular neck of the femoral component such that the axis of the trunion hole portion of the hemispherical portion and a neck axis of the femoral component are coincident, to represent a prosthetic joint center that is independently registered in the system; and
wherein the tracking device concurrently registers in the system the three dimensional positions of the femoral and acetabular components, the prosthetic joint center and the native anatomical joint center, respectively, to intraoperatively represent alterations in three dimensional location of the leg length and offset prior to any reduction of the prosthetic joint.

11. The system of claim 10 wherein the hemispherical portion is attached to the handle via a reproducible fixation, the geometry of the hemispherical portion being known with respect to the third three-dimensional dynamic reference array.

12. A computer assisted surgical navigation system for registering the position of prosthetic hip joint components, the system comprising:
an acetabular cup component;
a femoral prosthetic component;
a first reference element applied to the pelvis that generates a first three-dimensional dynamic reference array, which is independently registered in the system;
a second reference element applied to the femur that generates a second three-dimensional dynamic reference array, which is independently registered in the system;
a three-dimensional dynamic reference point representing the native anatomical center that is independently registered in the system and derived from the first and second dynamic arrays;
a tracking device having a handle and a hemispherical portion with a center, which generates a third three-dimensional dynamic reference array independently registered in the system, the hemispherical portion being attached to the handle and precisely articulating with the acetabular cup component such that the center of the hemispherical portion of the device and the center of the acetabular component are coincident, the hemispherical portion or the handle having a tip portion that independently and precisely articulates with a stem of the femoral component such that the axis of the tip portion of the device and a stem axis of the femoral component are coincident, to represent a prosthetic joint center that is independently registered in the system; and
wherein the tracking device concurrently registers in the system the three dimensional positions of the femoral and acetabular components, the prosthetic joint center and the native anatomical joint center, respectively, to intraoperatively represent alterations in three dimensional location of the leg length and offset prior to any reduction of the prosthetic joint.

* * * * *